(12) United States Patent
Kiviranta et al.

(10) Patent No.: US 8,865,922 B2
(45) Date of Patent: Oct. 21, 2014

(54) METHOD OF TREATING TALL OIL PITCH

(75) Inventors: Esko Kiviranta, Rauma (FI); Juhani Saviainen, Rauma (FI); Mikko Rintola, Rauma (FI)

(73) Assignee: Forchem Oy, Rauma (FI)

( * ) Notice: Subject to any disclaimer, the term of this patent is extended or adjusted under 35 U.S.C. 154(b) by 204 days.

(21) Appl. No.: 13/637,007

(22) PCT Filed: Mar. 28, 2011

(86) PCT No.: PCT/FI2011/050257
§ 371 (c)(1),
(2), (4) Date: Oct. 25, 2012

(87) PCT Pub. No.: WO2011/117475
PCT Pub. Date: Sep. 29, 2011

(65) Prior Publication Data
US 2013/0041167 A1 Feb. 14, 2013

(30) Foreign Application Priority Data

Mar. 26, 2010 (FI) .................................. 20105307

(51) Int. Cl.
| | | |
|---|---|---|
| *C07C 51/09* | (2006.01) | |
| *C11C 3/00* | (2006.01) | |
| *C11C 1/04* | (2006.01) | |
| *C07J 9/00* | (2006.01) | |
| *C11B 13/00* | (2006.01) | |

(52) U.S. Cl.
CPC ............... *C11B 13/005* (2013.01); *C07C 51/09* (2013.01); *C11C 3/003* (2013.01); *C11C 1/04* (2013.01); *C07J 9/00* (2013.01)
USPC ........... 554/167; 554/161; 554/163; 554/165; 530/205; 560/129

(58) Field of Classification Search
CPC ........... C11B 13/005; C07C 51/09; C07J 9/00
See application file for complete search history.

(56) References Cited

U.S. PATENT DOCUMENTS

| 4,524,024 A * | 6/1985 | Hughes ......................... 530/205 |
| 2011/0082307 A1 * | 4/2011 | Stigsson et al. ............... 552/541 |

FOREIGN PATENT DOCUMENTS

| FI | 118007 B1 | 5/2007 |
| WO | WO-2008139041 A1 | 11/2008 |
| WO | WO-2009125072 A1 | 10/2009 |

OTHER PUBLICATIONS

Holmbom, B., Composition of Tall Oil Pitch, Mar. 1978, Journal of the American Oil Chemists' Society, vol. 55, issue 3, pp. 342-344.*

* cited by examiner

*Primary Examiner* — Yate K Cutliff
(74) *Attorney, Agent, or Firm* — Birch, Stewart, Kolasch & Birch, LLP

(57) ABSTRACT

A method of treating tall oil pitch, which comprises sterol esters of fatty acids. According to the present invention, the esters of sterols and fatty acids are broken down, in which case especially formic acid esters or acetic acid esters of sterols are formed instead. The free fatty acids and sterol esters generated are distilled or separated in another way. Use of the present invention increases the yield of fatty acids and also facilitates the separation of sterols from tall oil pitch.

15 Claims, 1 Drawing Sheet

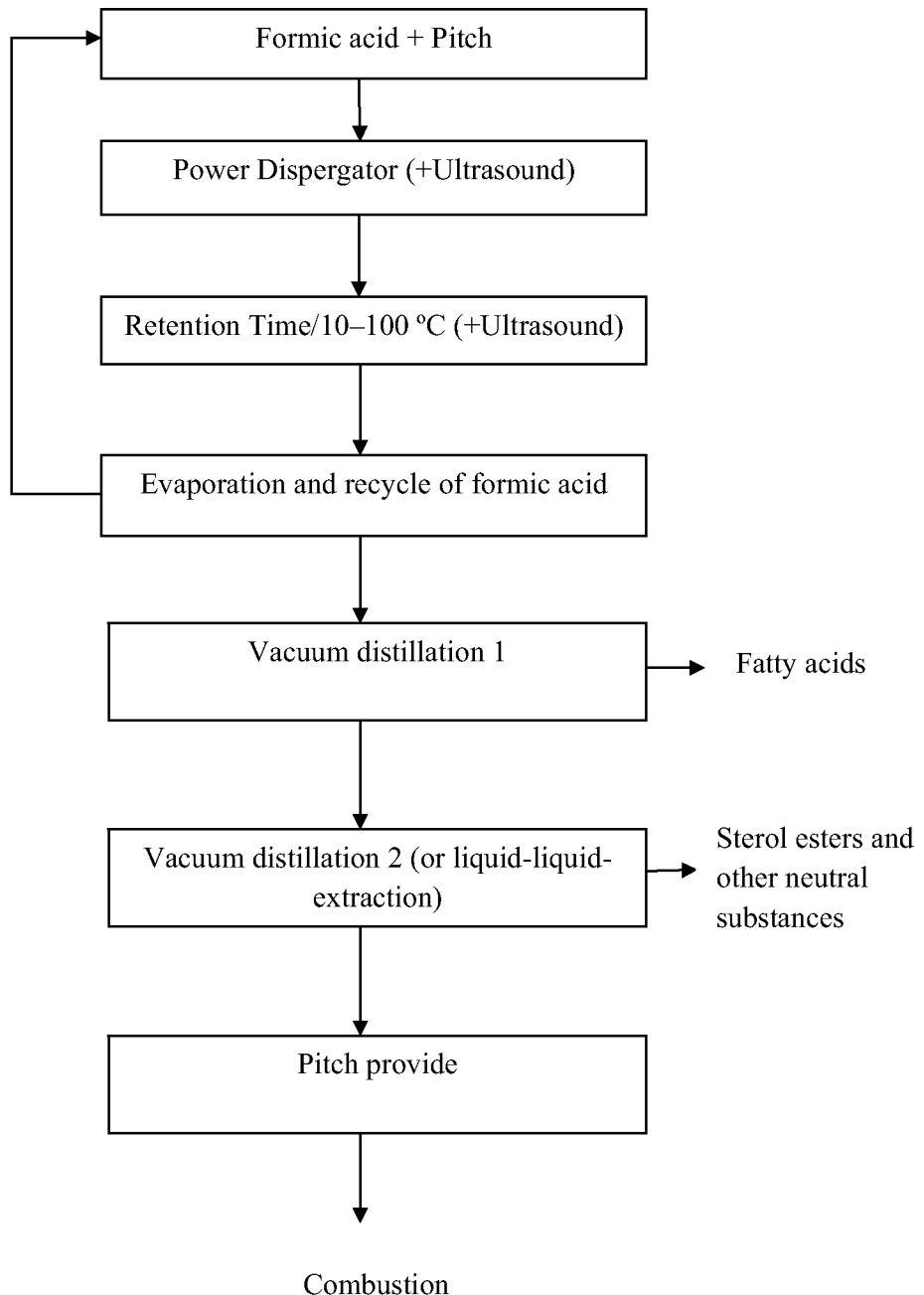

METHOD OF TREATING TALL OIL PITCH

This application is the National Phase Under 35 U.S,C. §371 of PCT International Application No. PCT/FI2011/050257 which has an International filing date of Mar. 28, 2011, which claims priority to Finnish Application No. 20105307 filed on Mar. 26, 2010. The entire contents of all applications listed above are hereby incorporated by reference.

The present invention relates to a method of treating tall oil pitch, according to the preamble of Claim 1.

According to a method such as this, at least part of the fatty acid esters of a tall oil pitch composition, which comprises sterol esters of fatty acids and possibly free sterols or other wood alcohols (i.e. compounds which comprise hydroxyl groups), are decomposed in order to modify the tall oil pitch, and from the pitch thus obtained, the fatty acid residues are recovered, either as acids or as new esters.

As a by-product in the cellulose industry, tall oil is generated approximately 80-30 kg/tonne of pulp, more generally on average 50 kg/tonne. "Tall oil", which is an extractive sourced from spruce and birch, too, is comprised of resin acids, fatty acids, neutral materials, i.e. mainly sterols, and esters of these alcohols and acids.

Tall oil is generally refined by distillation at a low pressure. Primary oil, fatty acids and resin acids are recovered as a surplus of the distillation, and tall oil pitch is generated as a distillation residue.

The word "pitch" originates from the fact that there is a large quantity of dimers and other oligomers, too, in the pitch and, consequently, it is not easy to separate components from it by distillation. The quantity of pitch is typically approximately 20-35% of the tall oil input into the distillery. A pitch such as this comprises approximately 3-5% of free fatty acids, 7-14% of free resin acids, 35-40% of fatty acid esters, mainly as sitosterol esters, and other neutral materials approximately 40%. The presented percentages are calculated from the weight of the composition. When the total quantity of fatty acids is approximately 20%, the most part of it is bound as esters; fatty acids form esters mainly with sterols.

Tall oil pitch is mainly used as a fuel, such as heavy petroleum-based fuel oil. The use of pitch is limited, firstly by its high viscosity (3000 cP/50° C.), and, secondly, by the fact that tall oil pitch is never totally rigid. Consequently, it is used in flaming torches and outdoor fire pots and similar objects. However, the fuel value of tall oil pitch is financially only a fraction of the value of the pure components, such as fatty acids and sterols, contained in it. For instance, the fatty acids alone are twice as expensive as pitch.

Recovery of the fatty acids from tall oil pitch is very important in the utilisation of pitch.

It is already known that it is possible to release the fatty acids from their esters by using hydrolysis, which is described, among others, in U.S. Pat. No. 2,058,574. However, the known solution relates to treatment of material other than tall oil pitch.

Releasing fatty acids from their esters is described in U.S. Pat. No. 5,097,012, too. According to this patent, fatty acids are hydrolysed and extracted, and they are separated by using pure water at a temperature at which they are converted into a form that is soluble in water, i.e. at a temperature of approximately 250-360° C. and at a pressure of 40-86 bar.

It is possible to break down the sterol-fatty acid esters of tall oil pitch by using an alkali treatment, in which case the fatty acids become non-volatile in the distillation, and the sterols can be removed as alcohols from the mixture by distillation under a high vacuum. With regard to the known technology, we can refer to an international published patent application WO 01/98444 A2, by Resitec. According to this published patent application, alkali salts of a fatty acid are changed into Mg salts, which salts have a lower melting point than Na salts. According to another alternative, tall oil pitch is treated directly with MgO, in which case a liquid fatty acid salt is generated and the sterols and other similar neutral materials are easily removed by distillation under a vacuum.

It is an aim of the present invention to provide a new way of recovering fatty acids from tall oil pitch.

The new invention relates firstly to treatment of pitch which is generated in a tall oil distillery but, at the same time, it is possible to apply the invention to tall oil pitch bought from other sources and treated in the way described in the present invention.

In the pitch, almost all the fatty acids are esterified at the high temperatures that occur in the process of distillation, and also prior to that, during storage of the crude tall oil.

It should be noted that the average molecular weight of the fatty acids is approximately 282 and, when the molecular weight of, for instance, β-sitosterol is 414, the molecular weight of their mutual ester will be 678. Thus, it is understandable that further distillation of pitch is not possible at a reasonably high vacuum and at a reasonably high temperature.

In FI Patent No. 120540, crude tall oil is treated with a small-molecular organic acid, which prevents large-molecular fatty acids from esterifying the sterols, by first carrying out protective esterification of them by using a small-molecular organic acid.

In the present invention, the same property of a small-molecular organic acid is used, but in another way. The new way is transesterification, by which the esters of sterols of tall oil pitch and the esters of fatty acids are cleaved, in which case especially carboxylic acid esters of sterols, typically esters of formic acid or acetic acid, are formed instead. The free fatty acids and sterol esters obtained are easily distilled. In this way it is possible later, at a much lower pressure, to separate the reaction products from the rest of the pitch by distillation, both as fatty acids and as sterol formates or sterol acetates.

More specifically, the method according to the present invention is mainly characterized by what is stated in the preamble of Claim 1.

Considerable advantages are achieved with the present invention. Thus, the yield of fatty acids is increased by the present invention, and also the separation of sterols from tall oil pitch is facilitated.

In the following, the present invention will be examined in more detail with the help of a detailed explanation and some non-limiting working examples.

As described above, according to the present solution, tall oil pitch which comprises sterols esters of fatty acids and possibly free wood alcohols (not sterols) is treated by forming sterol esters with lower alkanoic acids. At the same time, the fatty acids are released from their esters.

In fact, it is possible to carry out the esterification in many ways. According to one preferred embodiment, the esters of fatty acids of the tall oil pitch are transesterified by using a lower alkanoic acid or by using an ester of a lower alkanoic acid. Correspondingly, free sterols and other wood alcohols which possibly are present in the tall oil pitch, are esterified with a lower alkanoic acid or with a reactive derivative of a lower alkanoic acid.

Most suitably, the esterification is initiated in a mixing zone, in which large shear forces are directed at the mixture of acid and pitch, in order to disperse the tall oil pitch into an aqueous solution of at least one lower carboxylic acid or, correspondingly, to disperse and mix the tall oil pitch in at least one lower carboxylic acid.

Because pitch is a very viscous material, large shear forces or high acceleration must be used when treating it. The means which bring about an efficient dispersion are a power mixer or/and ultrasound.

Large shear forces are preferably generated by using a power mixer which has several sequential shear zones (below also called a "multi-stage power mixer"). Here, shear zones mean "blades" which pass close to each other and between which large shear forces are generated in the intermediate material. Examples of such devices are "Cavitron" (supplier: vom Hagen Funke GmbH) and "Condux Universal Mills" (supplier: Netzsch-Condux Mahltechnik GmbH). The energy needed for mixing and for the generation of shear forces is at least 2.5 kWh/tonne of raw material mixture, preferably 5-7 kWh/tonne of raw material mixture.

According to another embodiment, the large shear forces are generated at least partly by ultrasound. It is also possible to use ultrasound together with a power mixer or arranged in series with such a power mixer. Preferably, the transesterification is almost completed or even totally completed by ultrasound. More preferably, the entire transesterification can be accelerated with the help of ultrasound.

According to published studies, it is possible, by using ultrasound, to accelerate by as much as 19 times the processes of esterification (Ultrasonics Sonochemistry Volume 14, Issue 2, February 2007, pp 213-218).

The accompanying drawing (FIG. 1) shows the flow diagram of one embodiment.

In the first stage, a mixture is generated of pitch and a lower carboxylic acid, which mixture is then dispersed with, for instance, a power dispergator. It is possible to intensify the dispersion with ultrasound. Typically, alkanoic acid (in practice a lower carboxylic acid) is dispersed into the pitch, at a temperature of approximately 20-200° C., for instance 90-200° C. The lower alkanoic acid used is $C_{1-4}$ carboxylic acid, especially formic acid or acetic acid. The lower alkanoic acid ester used is $C_{1-4}$ alkyl ester, especially methyl or ethyl ester.

There are certain preferable optional phases which can be used in the first stage.

Thus, the carboxylic acid can comprise at least some water, most suitably approximately 1-40% by volume, especially approximately 5-25% by volume. According to one embodiment, the solvent which is present in the transesterification is methyl formate or methyl acetate, together with the corresponding carboxylic acids.

These applications indicate the following: also a small amount of hydrolysis occurs in the formic acid or acetic acid treatment, because—as described above—for instance a typical industrial formic acid comprises 5-15% of water (acetic acid slightly less). Thus, the reaction mixture also comprises a small quantity of fatty acids which are released by the hydrolysis. It is possible to only emulsify the formic acid-water solution into molten tall oil pitch. However, if methyl formate is brought in, too, a partly homogeneous phase is generated, in which the esterification takes place more easily and in which the methyl formate acts as a transesterification agent, too.

The generated mixture is allowed to settle. The retention time is approximately 1-168 h and the temperature approximately 10-100° C., especially approximately 20-30° C.

The breaking down of an ester has a direct effect on the separation process. The molecular weight of sterol oleate is, for instance, 678 and of oleic acid 282.

Hence, the distillability of an ester varies greatly depending on its molecular weight. For instance, the vapour pressure of oleic acid is approximately 30 kPa at a temperature of 327° C., and when, correspondingly, the vapour pressure of sitosterol is 0.1 kPa, the molecular weight of sitosterol is 414. Although the vapour pressures and the consequent distillabilities do not directly follow the molecular weight, this molecular weight is very important. For instance, the effect of formic acid on the molecular weight is only 30 units.

In practice, alkanoic acid treatment, especially formic acid treatment, is carried out using a molar surplus (most suitably the carboxylic acid surplus is approximately 1.1-20 times larger, with regard to the acid groups, than the hydroxyl groups of sterols.

The stirring during the treatment is so efficient that the pitch is totally dispersed into the aqueous solution of formic acid or, vice versa, depending on the volumetric ratio between the pitch and the formic acid solution. It is possible to work either under pressurised or non-pressurised (i.e. at normal pressure) conditions, preferably at a temperature of 50-100° C. It is also possible to use a higher temperature (approximately 100-250° C.) and a corresponding pressure (1-20 bar abs.).

As mentioned above, an alternative is that the free sterols and other wood alcohols contained in the pitch can be also transesterified by using esters of lower alkanoic acids, such as methyl or ethyl formate. In this case, it is possible to encourage the reaction by choosing the conditions in such a way that the alcohol, which is generated in the reaction, is removed from the reaction mixture and thus the balance of the reaction is shifted in favour of the desired reaction products.

After the treatment, it is possible to remove by distillation the formic acid surplus and the water from the mixture. This can be carried out immediately after the treatment. Preferably, the acid is recycled to the beginning of the process.

In the next treatment, both the fatty acids and the sterol formate esters are distilled. Depending on the initial material, the distillation is always carried out at the most appropriate different pressures and temperatures. Material of high-molecular weight remains in the distillation residue. If also methyl formate has been used, at the same time this is distilled as a back flow (boiling point +32° C.).

Other separation methods can be used, too, if transesterification of the sterol-fatty acid esters is carried out by means of small-molecular carboxylic acids, and also if the esterification is carried out by using, for instance, methyl carboxylates.

Examples of alternative separation methods are precipitation of fatty acids such as Ca salts, and using organic solutions to extract other components. It is also possible to neutralise the fatty acids with NaOH, in which case they become soluble in water (10% solubility 25° C.).

The sterols, in turn, can be evaporated from the pitch after the fatty acids have been neutralised by using for instance MgO (as described in the Resitec patent).

After the fatty acids have been removed by distillation, it is possible to extract the sterols by means of a polar solvent, after the entire residue is first dissolved in a non-polar solvent. As regards the separation/recovery method used, we refer to, for instance, U.S. Pat. No. 4,044,031.

The method described above is related to a method of treating wood oil, according to FI patent 120540 (Forchem), but in this case, the treated tall oil pitch can be bought from other refiners, for instance.

The treatment of sterol esters and other neutral materials is a separation process per se, in which other operations can be carried out, too, but which are not related to the present invention.

EXAMPLE 1

Tall oil pitch was heated in a flow-through heat exchanger to a temperature of 96° C., and an 85 per cent formic acid, which had been heated to a temperature of 100° C., was pumped into the pitch by using a dosing pump. The ratio of the pitch to the formic acid was 1000 kg:51 kg, in which case the molar amount of formic acid was approximately twice as large as the molar amount of fatty acids contained in the pitch.

The flows were combined and treated with a Cavitron power mixer, in which case it was possible to emulgate the formic acid into the pitch.

The mixture was left to stand for approximately 44 hours, during which time it was stiffed slowly, and after which it was distilled in a thin film evaporator, in which case the water and the excess formic acid were removed by separation.

The conversion of the transesterification of the fatty acids was approximately 80%, as indicated by the yield of fatty acids in the vacuum distillation.

EXAMPLE 2

The same experiment was carried out as in example 1, but now at a laboratory scale, using a Bamix domestic mixer, which was operated at 10 000 rpm, and the diameter of the mixing blade was 3.6 cm, and the power 160 W.

The mixing was carried out for a period of 6 minutes in a 500 mm decanter. The mixture, still in the same decanter, was placed in an ultrasound bath for a period of 5 minutes and then moved to a heating chamber for a period of 2 hours (100° C.). The water was removed by evaporation and the fatty acids were distilled at a temperature of 285° C. and at a pressure of 1 mmHg. The conversion calculated was 85%.

The invention claimed is:

1. A method of treating tall oil pitch, which comprises sterol esters of fatty acids and possibly free wood alcohols, according to which method
decomposing at least part of the fatty acid esters of tall oil pitch,
recovering the fatty acid residues from the pitch
forming esters from the sterols of the fatty acid esters and from any free wood alcohols with lower alkanoic acids in order to release the fatty acids from their esters, and
recovering the free fatty acids and, optionally, the sterol esters.

2. The method according to claim 1, wherein the esters of the fatty acids of the tall oil pitch are transesterified by a lower alkanoic acid or by an ester of a lower alkanoic acid, and the free wood alcohols, which may be present in the tall oil pitch, are esterified by a lower alkanoic acid or transesterified by an ester of a lower alkanoic acid.

3. A method according to claim 1, wherein the esterification is initiated by large shear forces in order to disperse the tall oil pitch into an aqueous solution of at least one lower carboxylic acid or, correspondingly, to disperse the tall oil pitch and mix it in at least one lower carboxylic acid.

4. The method according to claim 3, wherein the large shear forces are generated by a multi-stage power mixer.

5. A method according to claim 3, wherein the large shear forces are generated at least partly by ultrasound.

6. A method according to claim 1, wherein the transesterification reaction is almost completed by ultrasound.

7. A method according to claim 1, wherein the pitch is dispersed at a temperature of 20-200° C. into carboxylic acid.

8. A method according to claim 1, wherein the lower alkanoic acid used is $C_{1-4}$ carboxylic acid.

9. A method according to claim 1, wherein the ester of a lower alkanoic acid used is $C_{1-4}$ alkyl ester.

10. A method according to claim 1, wherein the solvent, which is included in the transesterification, is methyl formate or methyl acetate, together with the corresponding carboxylic acids.

11. The method according to claim 7, wherein said carboxylic acid comprises water.

12. The method according to claim 11, wherein said carboxylic acid comprises approximately 1-40% water by volume.

13. The method according to claim 11, wherein said carboxylic acid comprises approximately 5-25% water by volume.

14. The method according to claim 8, wherein said carboxylic acid is formic acid or acetic acid.

15. The method according to claim 9, wherein said $C_{1-4}$ alkyl ester is methyl or ethyl ester.

* * * * *